(12) United States Patent
Buck et al.

(10) Patent No.: US 10,096,383 B2
(45) Date of Patent: Oct. 9, 2018

(54) PERFORMING A HEALTH ANALYSIS USING A SMART FLOOR MAT

(71) Applicant: International Business Machines Corporation, Armonk, NY (US)

(72) Inventors: Alexander J. Buck, Austin, TX (US); Alyson T. Cabral, Austin, TX (US); Karl J. Weinmeister, Austin, TX (US); Brian L. White Eagle, Austin, TX (US); James Xenidis, Cedar Park, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/950,702

(22) Filed: Nov. 24, 2015

(65) Prior Publication Data
US 2017/0147767 A1   May 25, 2017

(51) Int. Cl.
  *G06Q 50/00*   (2012.01)
  *G16H 50/20*   (2018.01)
  *G06F 19/00*   (2018.01)

(52) U.S. Cl.
  CPC .......... *G16H 50/20* (2018.01); *G06F 19/324* (2013.01); *G06F 19/345* (2013.01)

(58) Field of Classification Search
  CPC ............................... G06Q 50/22; G06Q 50/24
  See application file for complete search history.

(56) References Cited

U.S. PATENT DOCUMENTS 5,821,871 A * 10/1998 Benzler .............. G07C 9/00039
                                                              235/382
8,460,220 B2    6/2013 Cuddihy
                (Continued)

FOREIGN PATENT DOCUMENTS

EP        2197407 A1    6/2010

OTHER PUBLICATIONS

Qian et al., "People Identification Using Gait via Floor Pressure Sensing and Analysis", D. Roggen et al. (Eds.): EuroSSC 2008, LNCS 5279, pp. 83-98, 2008.
(Continued)

*Primary Examiner* — Lena Najarian
(74) *Attorney, Agent, or Firm* — John R. Pivnichny; Hunter E. Webb; Keohane & D'Alessandro PLLC

(57) ABSTRACT

Approaches presented herein enable performing a health analysis of a user using a smart floor mat. Specifically, a sensory array of the smart floor mat collects static and dynamic pressure data for capturing the movement and force exerted by a user's feet as the user walks across the smart floor mat. A healthcare analysis is then performed by comparing this current measurement data against the user's historical measurement data and expected results to generate a healthcare insight such as a trend, pattern, or deviation. The healthcare insight can predict or indicate a health issue. If a deviation exceeding a predefined permissible threshold exists, a healthcare professional can be notified.

5 Claims, 5 Drawing Sheets

(56) References Cited

U.S. PATENT DOCUMENTS

| | | | |
|---|---|---|---|
| 9,036,019 B2 | 5/2015 | Hanson et al. | |
| 2006/0005041 A1* | 1/2006 | Lazeroms | A61B 5/1036 713/186 |
| 2007/0255186 A1* | 11/2007 | Grill | A61H 3/00 600/595 |
| 2008/0292179 A1* | 11/2008 | Busch | A43B 17/00 382/154 |
| 2012/0148115 A1* | 6/2012 | Birdwell | G06K 9/00 382/116 |
| 2012/0289866 A1 | 11/2012 | Irby et al. | |
| 2013/0012788 A1* | 1/2013 | Horseman | G06F 19/3418 600/301 |
| 2013/0046149 A1* | 2/2013 | Gettelman | A61B 5/744 600/301 |
| 2014/0039657 A1 | 2/2014 | Spector | |
| 2014/0180171 A1 | 6/2014 | Hyde et al. | |
| 2014/0224867 A1* | 8/2014 | Werner | G06Q 30/0623 235/375 |
| 2015/0105631 A1 | 4/2015 | Tran et al. | |
| 2015/0320352 A1* | 11/2015 | Ben Shalom | A61B 5/1036 600/587 |
| 2015/0351484 A1* | 12/2015 | Rubin | G01G 3/14 36/43 |
| 2016/0066820 A1* | 3/2016 | Sales | A61B 5/1114 600/595 |

OTHER PUBLICATIONS

Orr et al., "The Smart Floor: A Mechanism for Natural User Identification and Tracking", ACM, Apr. 1, 2000, 9 pages.

"IDC Presents U.S. Internet of Things Spending Guide for Eight Vertical Markets", http://www.idc.com/getdoc.jsp?containerId=prUS24851214, May 12, 2014, 2 pages.

"HR Mat", https://www.tekscan.com/products-solutions/systems/hr-mat, Oct. 1, 2015, 4 pages.

Wolfson et al., "Gait Assessment in the Elderly: A Gait Abnormality Rating Scale and Its Relation to Falls", Oxford Journals, Journal of Gerontology, vol. 45, Issue 1, Nov. 15, 1988, 2 pages.

Do et al., "Gait Analysis Using Floor Markers and Inertial Sensors", http://www.ncbi.nlm.nih.gov/pmc/articles/PMC3304129/, Dec. 1, 2011, 14 pages.

Muro-De-La-Harran et al., "Gait Analysis Methods: An Overview of Wearable and Non-Wearable Systems, Highlighting Clinical Applications", Sensors 2014, 33 pages.

"Floor Sensor Pad", http://notifex.com/products/floor-pad-sensor/, Jun. 29, 2013, 1 page.

Middleton et al., "A floor sensor system for gait recognition", Automatic Identification Advanced Technologies, 2005, Fourth IEEE Workshop, Oct. 17, 2005, 6 pages.

\* cited by examiner

PERFORMING A HEALTH ANALYSIS USING A SMART FLOOR MAT

TECHNICAL FIELD

This invention relates generally to health monitoring and, more specifically, to gathering measurement data over time while a user walks on a smart floor mat apparatus, performing a health analysis on the measurement data by comparing to expected results and generating a healthcare insight based on the results of the health analysis.

BACKGROUND

Smart technology has come to represent different things to different people. The definition usually depends on the product being described. In principle, smart technology is about getting performance improvements out of everything from electric grids and transportation networks to water supply systems and health care services by trying to align constrained supply with erratic demand more systematically. In practice, smart technology is mostly about harnessing a combination of information technology products (sensors, monitoring systems, automated controls, modeling, and other decision-support applications) more intelligently.

While still in its infancy, the number of smart home products, such as devices that let a person control a home's lighting, thermostat, or a home's appliance from a smart phone, is rapidly growing. Emerging smart technologies are simplifying tasks, making better use of resources, and transforming the way people live. Health-focused applications for smart homes are also becoming increasingly popular. Traditional smart home technology combined with new monitoring technologies may prevent falls in an increasingly aging population and detect health status changes among individuals of all ages in an effort to increase optimal health and longevity.

SUMMARY

In general, embodiments described herein provide approaches for performing a health analysis of a user using a smart floor mat. Specifically, a sensory array of the smart floor mat collects static and dynamic pressure data for capturing the movement and force exerted by a user's feet as the user walks across the smart floor mat. A healthcare analysis is then performed by comparing this current measurement data against the user's historical measurement data and expected results to generate a healthcare insight such as a trend, pattern, or deviation. The healthcare insight can predict or indicate a health issue. If a deviation exceeding a predefined permissible threshold exists, a healthcare professional can be notified.

One aspect of the present invention includes a computer-implemented method for performing a health analysis of a user, comprising: receiving, from a smart floor mat having a sensory array, current measurement data associated with the user, wherein the sensory array collects current measurement data as the user walks across the smart floor mat; retrieving a set of expected results from an expected results database; performing a health analysis using the current measurement data and the set of expected results; and generating a healthcare insight based on the health analysis.

Another aspect of the present invention includes a computer system for performing a health analysis of a user, the computer system comprising: a memory medium comprising program instructions; a bus coupled to the memory medium; and a processor for executing the program instructions, the instructions causing the system to: receive, from a smart floor mat having a sensory array, current measurement data associated with the user, wherein the sensory array collects current measurement data as the user walks across the smart floor mat; retrieve a set of expected results from an expected results database; perform a health analysis using the current measurement data and the set of expected results; and generate a healthcare insight based on the health analysis.

Yet another aspect of the present invention includes a computer program product for performing a health analysis of a user, the computer program product comprising a computer readable storage device, and program instructions stored on the computer readable storage device, to: receive, from a smart floor mat having a sensory array, current measurement data associated with the user, wherein the sensory array collects current measurement data as the user walks across the smart floor mat; retrieve a set of expected results from an expected results database; perform a health analysis using the current measurement data and the set of expected results; and generate a healthcare insight based on the health analysis.

Yet still another aspect of the present invention includes a method for facilitating a health analysis of a user, comprising: providing a computer infrastructure that includes at least one computer device that operates to perform the steps of: receive, from a smart floor mat having a sensory array, current measurement data associated with the user, wherein the sensory array collects current measurement data as the user walks across the smart floor mat; retrieve a set of expected results from an expected results database; perform a health analysis using the current measurement data and the set of expected results; and generate a healthcare insight based on the health analysis.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings in which.

Figure 1:
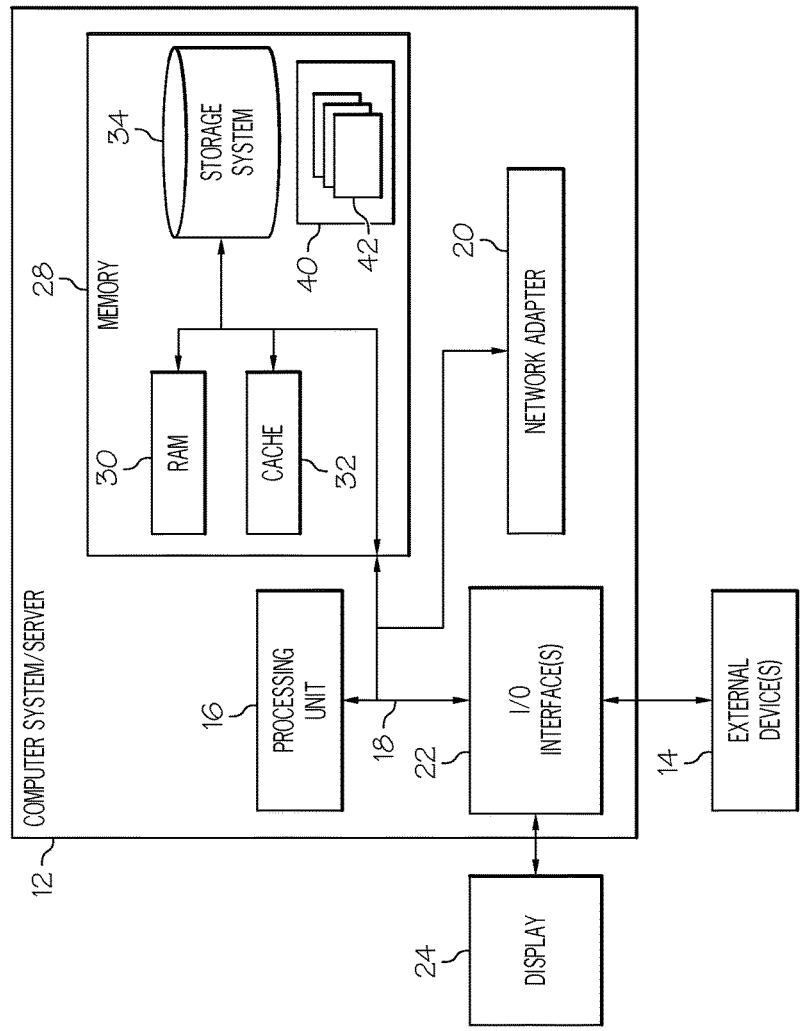
FIG. 1 shows an architecture 10 in which the present invention may be implemented according to illustrative embodiments.

The drawings are not necessarily to scale. The drawings are merely representations, not intended to portray specific parameters of the invention. The drawings are intended to depict only typical embodiments of the invention, and therefore should not be considered as limiting in scope. In the drawings, like numbering represents like elements.

DETAILED DESCRIPTION

Illustrative embodiments will now be described more fully herein with reference to the accompanying drawings, in which illustrative embodiments are shown. It will be appreciated that this disclosure may be embodied in many different forms and should not be construed as limited to the illustrative embodiments set forth herein. Rather, these embodiments are provided so that this disclosure will be thorough and complete and will fully convey the scope of this disclosure to those skilled in the art.

Furthermore, the terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. Furthermore, similar elements in different figures may be assigned similar element numbers. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

Unless specifically stated otherwise, it may be appreciated that terms such as "processing," "detecting," "determining," "evaluating," "receiving," or the like, refer to the action and/or processes of a computer or computing system, or similar electronic data center device, that manipulates and/or transforms data represented as physical quantities (e.g., electronic) within the computing system's registers and/or memories into other data similarly represented as physical quantities within the computing system's memories, registers or other such information storage, transmission, or viewing devices. The embodiments are not limited in this context.

As stated above, embodiments described herein provide approaches for performing a health analysis of a user using a smart floor mat. Specifically, a sensory array of the smart floor mat collects static and dynamic pressure data for capturing the movement and force exerted by a user's feet as the user walks across the smart floor mat. A healthcare analysis is then performed by comparing this current measurement data against the user's historical measurement data and expected results to generate a healthcare insight such as a trend, pattern, or deviation. The healthcare insight can predict or indicate a health issue. If a deviation exceeding a predefined permissible threshold exists, a healthcare professional can be notified.

The inventors of the present invention have discovered that, with wearable technology and wearable devices becoming increasingly popular, smart objects may be the next step in smart technology. Smart objects are devices that collect data with minimal interference in the daily lives of users. Embodiments of the present invention provide a smart floor mat system which is not worn, and is multi-user. In an increasingly health-conscious and aging culture there is a desire to collect health data, allow users and their health care providers to monitor user health, and give health predictions. A smart object providing insight into health can be useful.

People increasingly want to monitor and improve their health without taking a trip to a doctor's office. Using sensory data to determine weight, foot size, flat footedness, gait, balance, and identity, over time, embodiments of the present invention are able to predict physical ailments, and/or show improvement with changes without being disruptive of everyday activity. The smart floor mat system described herein may be used by multiple users and is not battery constrained. In addition, when data is collected and aggregated from multiple smart floor mats representing a large pool of users, data scientists and health care providers can be able to distinguish valuable patterns in the floor sensor data that give insight to medical aliments and improved treatment plans.

Embodiments of the present invention can provide data on a user's gait, weight and movement characteristics. By detecting how people move throughout a space over time, there is a huge potential for health analysis. A person's gait, weight, and movement analysis may indicate medical conditions and diseases such as arthritis, shin splints, Parkinson's and cognitive diseases like Alzheimer's, among others. Traditionally, a trip to a doctor is necessary in order to get feedback on gait, imbalances, and the like. Because these trips occur infrequently, data points are few and far between. Analysis can be more accurate if data samples can be much more frequent (e.g., multiple times throughout a day). Today, diagnoses are frequently based on a single data point (e.g., a measurement in the doctor's office), whereas changes in weight, gait, and movement over time can be indicators of underlying causes in the form of medical aliments.

Referring now to FIG. 1, a computerized implementation 10 of an embodiment for performing a health analysis using a smart floor mat to generate a healthcare insight will be shown and described. Computerized implementation 10 is only one example of a suitable implementation and is not intended to suggest any limitation as to the scope of use or functionality of embodiments of the invention described herein. Regardless, computerized implementation 10 is capable of being implemented and/or performing any of the functionality set forth hereinabove.

In computerized implementation 10, there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

This is intended to demonstrate, among other things, that the present invention could be implemented within a network environment (e.g., the Internet, a wide area network (WAN), a local area network (LAN), a virtual private network (VPN), etc.), a cloud computing environment, a cellular network, or on a stand-alone computer system. Communication throughout the network can occur via any combination of various types of communication links. For example, the communication links can comprise addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer system 12 is intended to demonstrate that some or all of the components of implementation 10 could be deployed, managed, serviced, etc., by a service provider who offers to implement, deploy, and/or perform the functions of the present invention for others.

Computer system 12 is intended to represent any type of computer system that may be implemented in deploying/realizing the teachings recited herein. Computer system 12 may be described in the general context of computer system executable instructions, such as program modules, being executed by a computer system. Generally, program modules may include routines, programs, objects, components, logic, data structures, and so on, that perform particular tasks or implement particular abstract data types. In this particular example, computer system 12 represents an illustrative system for performing a health analysis using a smart floor mat to generate a healthcare insight. It should be understood that any other computers implemented under the present invention may have different components/software, but can perform similar functions.

Computer system 12 in computerized implementation 10 is shown in the form of a general-purpose computing device. The components of computer system 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Processing unit 16 refers, generally, to any apparatus that performs logic operations, computational tasks, control functions, etc. A processor may include one or more subsystems, components, and/or other processors. A processor will typically include various logic components that operate using a clock signal to latch data, advance logic states, synchronize computations and logic operations, and/or provide other timing functions. During operation, processing unit 16 collects and routes signals representing inputs and outputs between external devices 14 and input devices (not shown). The signals can be transmitted over a LAN and/or a WAN (e.g., T1, T3, 56 kb, X.25), broadband connections (ISDN, Frame Relay, ATM), wireless links (802.11, Bluetooth, etc.), and so on. In some embodiments, the signals may be encrypted using, for example, trusted key-pair encryption. Different systems may transmit information using different communication pathways, such as Ethernet or wireless networks, direct serial or parallel connections, USB, Firewire®, Bluetooth®, or other proprietary interfaces. (Firewire is a registered trademark of Apple Computer, Inc. Bluetooth is a registered trademark of Bluetooth Special Interest Group (SIG)).

In general, processing unit 16 executes computer program code, such as program code for performing a health analysis using a smart floor mat to generate a healthcare insight, which is stored in memory 28, storage system 34, and/or program/utility 40. While executing computer program code, processing unit 16 can read and/or write data to/from memory 28, storage system 34, and program/utility 40.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media, (e.g., VCRs, DVRs, RAID arrays, USB hard drives, optical disk recorders, flash storage devices, and/or any other data processing and storage elements for storing and/or processing data). By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM, or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program code embodied on a computer readable medium may be transmitted using any appropriate medium including, but not limited to, wireless, wireline, optical fiber cable, radio-frequency (RF), etc., or any suitable combination of the foregoing.

Program/utility 40, having a set (at least one) of program modules 42, may be stored in memory 28 by way of example, and not limitation. Memory 28 may also have an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a consumer to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
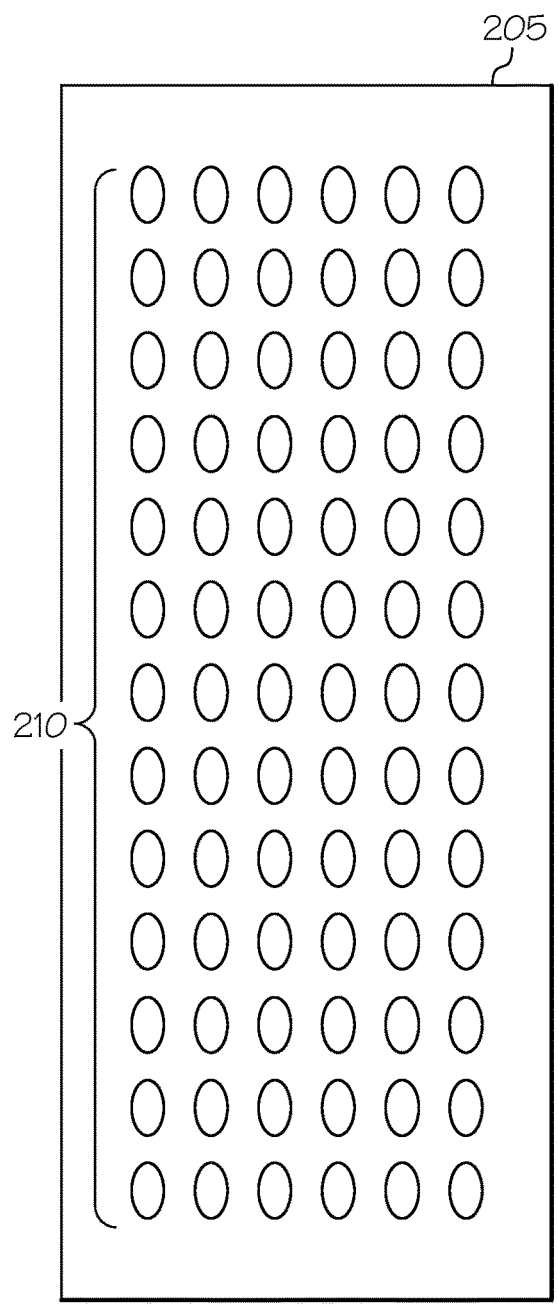
FIG. 2 shows an example smart floor mat diagram 200 including smart floor mat 205 having a sensory array 210 according to illustrative embodiments.

Referring now to FIG. 2, an example smart floor mat diagram 200 is shown. As shown, smart floor mat diagram 200 includes smart floor mat 205 having sensory array 210. Smart floor mat 205 may be made of ceramic, plastic, wood, carpet or any other appropriate material capable of including sensory array 210. Smart floor mat, can be implemented as a floor covering or, alternatively, can be integrated into the floor itself. Whatever the case, sensory array 210 may comprise a group of sensors (e.g., pressure sensors, force sensors, etc.) used for collecting and processing electromagnetic signals including pressure data. In a typical embodiment, the group of sensors of sensory array 210 may be deployed in a certain geometric pattern. As shown, smart floor mat 205 includes a sensory array 210 in a 6' by 13' sensor array pattern, although any a sensory array 210 containing any number of sensors deployed in any pattern or arrangement is envisioned. In any case, sensory array 210 can collect static and dynamic pressure data for capturing the movement and force exerted by a user's feet as the user walks across the smart floor mat 205. Smart floor mat 205 may be any size, but should be of sufficient length and width to provide meaningful measurement data.

In some embodiments, sensor array 210 can provide measurements of gait and balance through application interfaces (APIs) which can be used for detection of medical conditions. For the older population, elevated risk of fall due to balance issues presents a major risk while for patients having a neurological disease, gait is a marker for progress of the disease. Measurement data that the APIs can provide include, but are not limited to, a user identity, weight, foot size, degree of flat footedness, numerical description of gait, numerical description of balance, and the like. In one example, a user identity may be derived based on a weight and foot size of the user walking across smart floor mat 205. For example, a husband and wife (Joe and Jane) have smart floor mat 205 in a hallway of their home. User identities can be distinguished based on weight and foot size. In this example, Joe weighs 190 pounds and has foot size of men's 13. Jane only weighs 115 pounds and has a foot size of women's 9.

Figure 3:
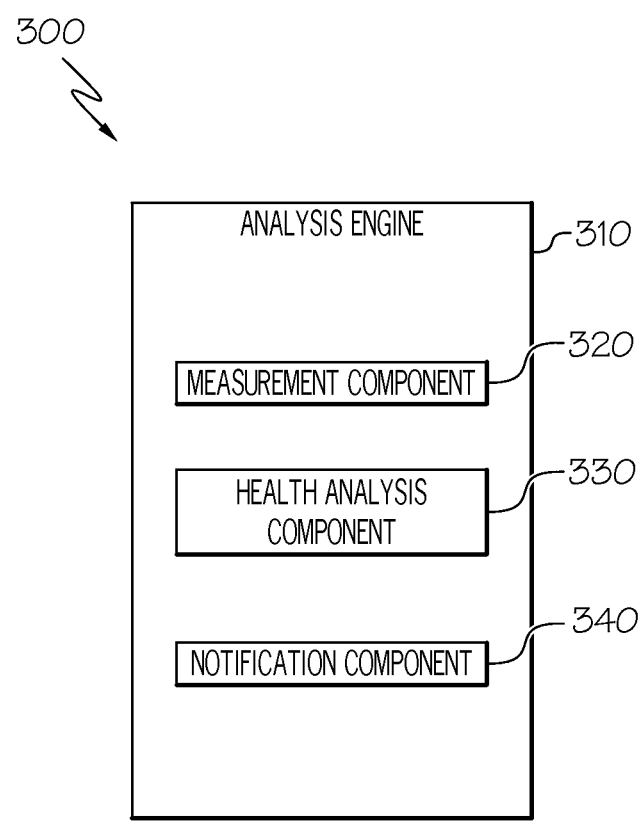
FIG. 3 shows a block diagram 300 that illustrates a system according to illustrative embodiments.

Referring now to FIG. 3, a block diagram 300 describing the functionality discussed herein according to an embodiment of the present invention is shown. It is understood that the teachings recited herein may be practiced within any type of computing environment (e.g., computer system 12). To this extent, the teachings recited herein may be practiced within a stand-alone computer system or within a networked computing environment (e.g., a client-server environment, peer-to-peer environment, distributed computing environment, cloud computing environment, and/or the like). If the teachings recited herein are practiced within a networked computing environment, each physical server need not have an analysis engine (hereinafter "system 310"). Rather, system 310 could be loaded on a server or server-capable device that communicates (e.g., wirelessly) with the physical server to provide beacon diagnosis therefor. Regardless, as depicted, system 310 can be implemented as program/utility 40 on computer system 12 of FIG. 1 and can enable the functions recited herein. It is further understood that system 310 may be incorporated within or work in conjunction with any type of system that receives, processes, and/or executes commands with respect to information technology (IT) resources in a networked computing environment. Such other system(s) have not been shown in FIG. 2 for brevity purposes.

Figure 4:
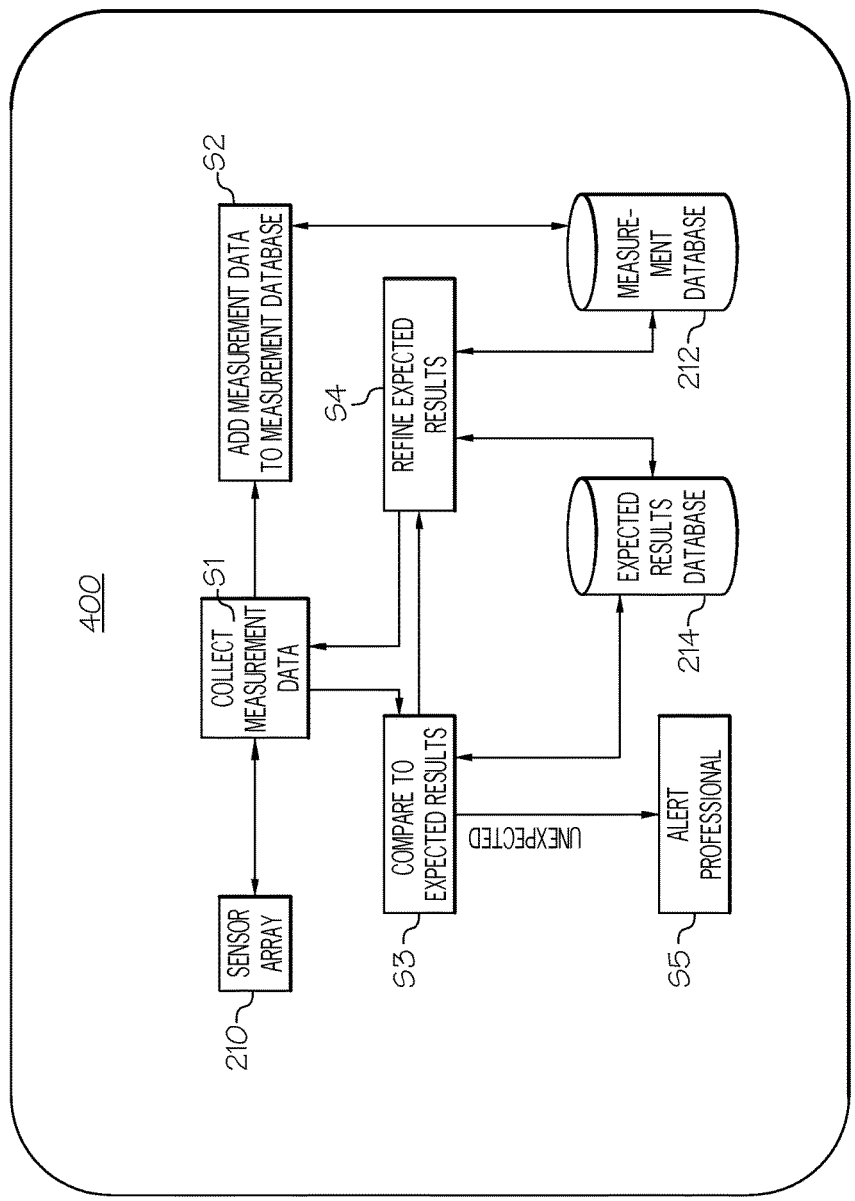
FIG. 4 shows a flow diagram 400 for performing a health analysis using a smart floor mat to generate a healthcare insight according to illustrative embodiments.

Referring now to FIG. 4 in conjunction with FIGS. 1-3, an example flow diagram 400 for performing a health analysis according to an embodiment of the invention is shown. At S1, sensory array 210 collects measurement data as a user walks the length of smart floor mat 205. As mentioned earlier, measurement data can include any objective measurements used for quantitative gait analysis including, but not limited to, a user identity, a weight of the user, a foot size of the user, a degree of user's flat footedness, a numerical description associated with the user's gait, or a numerical description associated with the user's balance.

Measurement component 320 of system 310, as executed by computer system/server 12, is configured to receive any measurement data collected by sensory array 210 of smart floor mat 205. For example, smart floor mat 205 is designed to transmit data measurements to measurement component 320 via data transmission. Data transmission may be performed, either by wire or wirelessly, in accordance with appropriate transmission principles known in the art, and data encryption may be employed if desired. Measurement data may be periodically received by measurement component 320 (e.g., when a user walks across smart floor mat 205), or may be pushed to measurement component 320 (e.g., nightly), or may be pulled to measurement component 320 (e.g., periodically, dynamically, randomly), or so forth. At S2, measurement data may be accumulated over a period of time and stored in measurement database 212 in order to accumulate quantitative gait analysis data to derive a historical gait pattern of a particular user.

Health analysis component 330 of system 310, as executed by computer system/server 12, is configured to analyze measurement data collected by measurement component 320 to assess a user's gait pattern in order to transform raw measurement data into healthcare insights such as trends, patterns, and deviations. Assessing a user's gait pattern can be useful for identifying particular areas of impairment and neurological defects affecting motor control. For example, information pertaining to an individual's particular gait pattern may generally be used to determine the existence of a physical impairment associated with weakened muscle development, limited range in the movement of joints, or poor posture. A user's gait pattern can be assessed in connection with pathological conditions such as cerebral palsy, multiple sclerosis, Parkinson's disease, and various other neuromuscular disorders. However, assessing a user's gait pattern is not only useful for identifying physical impairments and neurological diseases, but is also useful for monitoring the progress of rehabilitative measures and the recovery of a user after an injury or surgical procedure.

Various neurological diseases that affect motor control and gait possess unique identifiable characteristics. For example, in frontal lobe disease an individual is prone to small shuffling steps. As another example, an individual with Parkinson's disease is prone to small rapid steps, small backward steps after attempting to stop and difficultly turning quickly. In another example, a change in side-to-side weight distribution can indicate an injury on one side (e.g., hip injury, knee injury, etc.). These unique identifiable characteristics may be detected through analysis of collected measurement data. When properly assessed, a user's particular gait pattern can help guide caregivers in determining appropriate treatments and preventative measures to be implemented.

To assess a user's gait pattern, at S3, current measurement data acquired by measurement component 320 and expected results stored in expected results database 214 are made accessible to health analysis component 330 to execute a comparison and determine whether there is a deviation exceeding a predefined permissible threshold. Expected results may be derived from a user's historical measurement data, historical measurements of other individuals, medical studies, medical trials, medical research, medical professionals, and/or data scientists, among others. Expected results can be used to provide an acceptable gait pattern (e.g., stride length, stride speed, balance, etc.) range for a particular user.

Health analysis component 330 determines whether any measurements of the user's current measurement data exceed a predefined permissible threshold when compared to expected results. For example, a user may begin to walk in small shuffling steps. It is expected that an individual may begin to take smaller steps as he or she ages. However, when a deviation of the user's smaller steps exceeds a permissible threshold when compared to expected results, this may indicate a frontal lobe disease in the user.

If a deviation exceeding a permissible threshold is not detected, current measurement data is accumulated with expected results from expected results database 214 at S4 to refine expected results, furthering contributing to the derivation of the gait pattern of the user being monitored. The accumulation of measurement data stored at S2 is linked back to S4 to allow for ongoing comparison of incoming measurement data with previously accumulated expected results. Further, expected results of expected results database 214 may continually be refined by historical measurements of other individuals, medical trials and/or research, medical professionals, and data scientists, among others.

Notification component 340 of system 310, as executed by computer system/server 12, is configured perform a notification procedure when a deviation exceeding a permissible threshold is determined by health analysis component 330, at S5. For example, a user's stride length may indicate that the user's is beginning to walk in small shuffling steps. A person's normal stride length may be determined based on historical data. Some deviation may be expected (e.g., a person may take smaller steps in the morning when first waking up, etc.). However, a continued reduction in stride length greater than a predefined threshold (e.g., 15 percent decrease) may indicate an onset of a frontal lobe disease. Notification producers executed at S5 may include transmission of an alert notification (e.g., email message, text message, etc.) to a caregiver (e.g., healthcare professional, family member, etc.).

Figure 5:
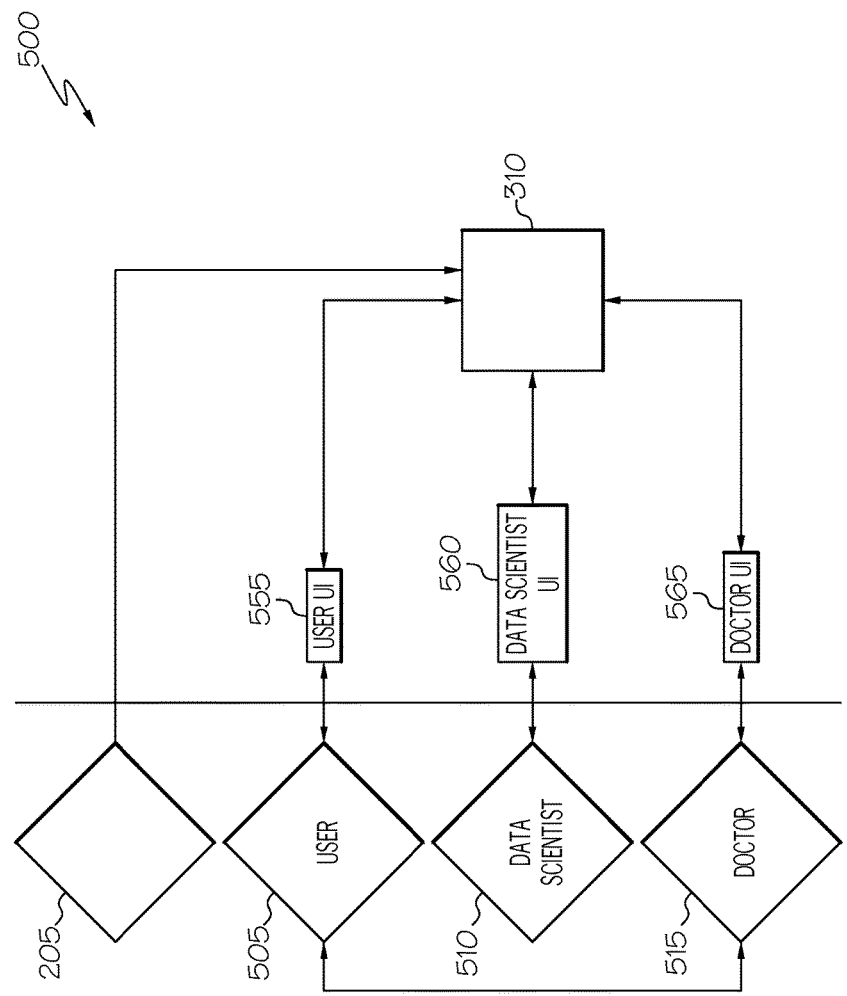
FIG. 5 shows a block diagram 500 describing the user interface functionality for displaying a healthcare insight according to illustrative embodiments.

FIG. 5 shows a block diagram 500 describing the user interface functionality for displaying a healthcare insight (e.g., trend, pattern, deviation, etc.) according to an embodiment of the present invention. As shown, block diagram 500 includes smart floor mat 205 having a sensory array 210, system 310, user 505 having an electronic device with user interface (UI) 555, data scientist 510 having an electronic device with data scientist UI 560, and doctor 515 having an electronic device with doctor UI 565. A suitable electronic device for communicating with system 310 may include, but is not limited to, a smart phone, a tablet computer, a laptop, and/or a desktop computer.

In an embodiment, using user UI 555, user 505 can view the user's historical measurement data, any health trends or patterns derived from the user's historical measurement data, and any feedback provided by a healthcare professional (e.g., doctor 515) based on the user's collected measurement data and expected results (e.g., correct drooping posture, etc.). Using doctor UI 565, doctor 515 (or other healthcare professional) can view a user's historical measurement data. Based on the user's historical measurement data, doctor 515 can determine any user trends or patterns (e.g., steps getting shorter, etc.), identify any potential health causes based on user patterns (e.g., possible onset of frontal lobe disease, etc.), and provide any feedback to user 505 (e.g., schedule a doctor appointment, etc.). Further, doctor 515 can speculate about any potential health causes based on trends across multiple users based on collected historical measurement data. Using data scientist UI 560, data scientist 510 can view measurement data of user 505 and/or others, perform any data cleansing (e.g., to be viewed by user 505 and/or doctor 515), and analyze historical measurement data to identify any trends or patterns across users.

As discussed, system 310 may perform a health analysis by comparing measurement data of a user to expected results. For example, Ernest, an elderly man, is struggling getting up and moving every day. He decides to place smart floor mat 205 in his bathroom so that he can monitor his movements throughout the day. Sensory array 210 collects measurement data each time Ernest walks across smart floor mat 205. Measurement data is received by measurement component 320. Health analysis component 330 compares the current measurement data with expected results. Based on the comparison and historical measurement data of others, doctor 515 notices a trend found that suggests cognitive decline. Ernest is tested for Alzheimer's disease and is treated early. His measurement data continues to be collected so that doctor 515 can determine how well any treatments for Ernest are working. The collected measurement data can be used to create personalized treatment plans for users.

In another example, Michael and Mary share an apartment. Mary was born with a medical condition in which one of her legs is slightly longer than the other. She decides to purchase smart floor mat 205 for their living room so that she can monitor how her condition is affecting her health. Michael also uses the living room so his data is also tracked. Gathered data from smart floor mat 205 alerts Michael that he has flat feet and should begin wearing orthotics. If he does not, doctor 515, who is monitoring Michael's measurement data, alerts Michael that he will begin to have issues with his right hip. Using user UI 555, gathered data allows Mary to see the trends in her condition and discovers her balance is worse than she thought. Based on her discovery and consultation with doctor 515, she decides surgery is her best option. Michael and Mary are able to live much healthier lives based on insights gained from using smart floor mat 205.

Referring back to FIG. 4, process flowchart 400 illustrates the architecture, functionality, and operation of possible implementations of systems, methods, and computer program products according to various embodiments of the present invention. In this regard, each block in the flowchart may represent a module, segment, or portion of code, which comprises one or more executable instructions for implementing the specified logical function(s). It should also be noted that, in some alternative implementations, the functions noted in the blocks might occur out of the order depicted in the figures. For example, two blocks shown in succession may, in fact, be executed substantially concurrently. It will also be noted that each block of flowchart illustration can be implemented by special purpose hardware-based systems that perform the specified functions or acts, or combinations of special purpose hardware and computer instructions.

Some of the functional components described in this specification have been labeled as systems or units in order to more particularly emphasize their implementation independence. For example, a system or unit may be implemented as a hardware circuit comprising custom VLSI circuits or gate arrays, off-the-shelf semiconductors such as logic chips, transistors, or other discrete components. A system or unit may also be implemented in programmable hardware devices such as field programmable gate arrays, programmable array logic, programmable logic devices or the like. A system or unit may also be implemented in software for execution by various types of processors. A system or unit or component of executable code may, for instance, comprise one or more physical or logical blocks of computer instructions, which may, for instance, be organized as an object, procedure, or function. Nevertheless, the executables of an identified system or unit need not be physically located together, but may comprise disparate instructions stored in different locations which, when joined logically together, comprise the system or unit and achieve the stated purpose for the system or unit.

Further, a system or unit of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices and disparate memory devices.

Furthermore, systems/units may also be implemented as a combination of software and one or more hardware devices. For instance, program/utility 40 may be embodied in the combination of a software executable code stored on a memory medium (e.g., memory storage device). In a further example, a system or unit may be the combination of a processor that operates on a set of operational data.

As noted above, some of the embodiments may be embodied in hardware. The hardware may be referenced as a hardware element. In general, a hardware element may refer to any hardware structures arranged to perform certain operations. In one embodiment, for example, the hardware elements may include any analog or digital electrical or electronic elements fabricated on a substrate. The fabrication may be performed using silicon-based integrated circuit (IC) techniques, such as complementary metal oxide semiconductor (CMOS), bipolar, and bipolar CMOS (BiCMOS) techniques, for example. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor devices, chips, microchips, chip sets, and so forth. However, the embodiments are not limited in this context.

Any of the components provided herein can be deployed, managed, serviced, etc., by a service provider that offers to deploy or integrate computing infrastructure with respect to a process for performing a health analysis using a smart floor mat to generate a healthcare insight. Thus, embodiments herein disclose a process for supporting computer infrastructure, comprising integrating, hosting, maintaining, and deploying computer-readable code into a computing system (e.g., computer system 12), wherein the code in combination with the computing system is capable of performing the functions described herein.

In another embodiment, the invention provides a method that performs the process steps of the invention on a subscription, advertising, and/or fee basis. That is, a service provider, such as a Solution Integrator, can offer to create, maintain, support, etc., a process for performing a health analysis using a smart floor mat to generate a healthcare insight. In this case, the service provider can create, maintain, support, etc., a computer infrastructure that performs the process steps of the invention for one or more customers. In return, the service provider can receive payment from the customer(s) under a subscription and/or fee agreement, and/or the service provider can receive payment from the sale of advertising content to one or more third parties.

Also noted above, some embodiments may be embodied in software. The software may be referenced as a software element. In general, a software element may refer to any software structures arranged to perform certain operations. In one embodiment, for example, the software elements may include program instructions and/or data adapted for execution by a hardware element, such as a processor. Program instructions may include an organized list of commands comprising words, values, or symbols arranged in a predetermined syntax that, when executed, may cause a processor to perform a corresponding set of operations.

The present invention may also be a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

It is apparent that there has been provided herein approaches for performing a health analysis using a smart floor mat to generate a healthcare insight. While the invention has been particularly shown and described in conjunction with exemplary embodiments, it will be appreciated that variations and modifications will occur to those skilled in the art. Therefore, it is to be understood that the appended claims are intended to cover all such modifications and changes that fall within the true spirit of the invention.

What is claimed is:

1. A smart floor mat system comprising:
   a smart floor mat installed in a residence of a user;
   a sensory array having a set of sensors within the smart floor mat that continuously measure current pressure measurement data that includes measurements of gait and balance of a user, a weight of the user, a foot size of the user, a degree of flat footedness associated with the user, a numerical description associated with the gait of the user, and a numerical description associated with the balance of the user as the user walks across the smart floor mat;
   a communication link within the smart floor mat; and
   a processor in communication with the smart floor mat over the communication link, the processor executing program instructions to:
      receive, from the communication link the current pressure measurement data associated with the user measured by the set of sensors in the sensory array;
      determine a user identity of the user based on the weight and the foot size;
      compare the current pressure measurement data with a set of expected results from an expected results database to determine whether the current pressure measurement data differs from the set of expected results by a predefined permissible threshold, the set of expected results being derived from historical measurement data having previously gathered measurements of the user measured by the set of sensors in the sensory array received over the communication link;
      combine the current pressure measurement data with the historical measurement data into a gait pattern trend;
      perform, in response to a determination that the current pressure measurement data differs from the set of expected results by the predefined permissible threshold, a health analysis based on a comparison of the gait pattern trend with a plurality of gait pattern trends indicative of different medical conditions; and
      generate an alert notification in response to the health analysis including a healthcare insight indicating a match with a gait pattern trend indicative of a particular medical condition.

2. The smart floor mat system of claim 1, further comprising program instructions to receive the historical measurement data associated with the user, wherein the healthcare insight includes a trend or pattern derived from at least one of: the current pressure measurement data, the historical measurement data, or the set of expected results.

3. The smart floor mat system of claim 2, further comprising program instructions to derive the permissible threshold from at least one of the historical measurement data associated with the user and the set of expected results.

4. The smart floor mat system of claim 3, wherein the healthcare insight includes a deviation of the gait and balance of the user exceeding the permissible threshold.

5. The smart floor mat system of claim 4, further comprising program instructions to generate the alert notification when the deviation exceeds the permissible threshold.

* * * * *